United States Patent [19]
Callard

[11] Patent Number: 5,703,670
[45] Date of Patent: Dec. 30, 1997

[54] EARPLUGS ADAPTED TO EYEGLASSES AND COMBINATION THEREOF

[76] Inventor: Shawn R. Callard, 2819 Swett Rd., Lyndonville, N.Y. 14098

[21] Appl. No.: 752,248

[22] Filed: Nov. 19, 1996

[51] Int. Cl.$^6$ ............................. G02C 5/14; G02C 1/00
[52] U.S. Cl. ........................................... 351/123; 351/158
[58] Field of Search ............................. 351/111, 118, 351/123, 158; 2/423, 209

[56] References Cited

U.S. PATENT DOCUMENTS

| | | | |
|---|---|---|---|
| 3,807,527 | 4/1974 | Sygnator | 351/123 |
| 3,943,925 | 3/1976 | Leight | 128/152 |
| 4,902,120 | 2/1990 | Weyer | 351/158 |
| 5,133,596 | 7/1992 | Korny et al. | 351/158 |
| 5,289,592 | 3/1994 | Paivarinta | 2/431 |
| 5,404,385 | 4/1995 | Ben-Haim | 377/24.2 |

FOREIGN PATENT DOCUMENTS

| 61536 | 3/1892 | Germany | 351/123 |
|---|---|---|---|

*Primary Examiner*—Huy Mai
*Attorney, Agent, or Firm*—Howard M. Ellis; Marianne Fuierer

[57] ABSTRACT

An earplug assembly adapted for joinder to eyeglass temples, preferably by means of an axial connector providing semirigid connection to one end of an elongated telescoping member for rotation in a single plane, an earplug being joined at the other end of the telescoping member for rotation in at least one plane containing the telescoping member, together with a combination comprising eyeglasses and the earplug assembly.

20 Claims, 5 Drawing Sheets

Fig. 2

EARPLUGS ADAPTED TO EYEGLASSES AND COMBINATION THEREOF

This invention is in the field of protective devices; more particularly, the invention relates to appliances for protecting the health and safety of personnel under circumstances in which eyeglasses and protective earplugs are worn.

BACKGROUND OF THE INVENTION

Many industries require their workers to wear protective earplugs, and a number of industries require their employees to wear both safety eyeglasses and protective earplugs. Such industries include, e.g., steel mills, stamping mills, foundries, machine shops, metal fabricators, and automotive repair facilities, such as body shops. Ensuring worker compliance with rules requiring these safety and protective appliances has always been difficult.

Eyeglasses can become quite uncomfortable after a period of time, especially if they slide down the wearer's nose and have to be pushed back into position frequently. The perspiration commonly generated by a worker on the job exacerbates the tendency of the eyeglasses to slide.

Earplugs can also become uncomfortable if worn for extended periods of time, and unless they fit properly and completely seal the external auditory canal, they don't protect against noise very well. Moreover, in a number of jobs, one or the other of these safety appliances may not be needed simultaneously all the time, and the unused appliance is easily misplaced when not being used.

Safety eyeglasses are typically provided by the employer, and the employer's desire to minimize his inventory of the different sizes of eyeglasses needed to fit various workers has provided an impetus for eyeglasses manufacturers to make them adjustable, at least as to the length of the temples of the eyeglasses.

Several attempts have been made over the years to tie these two safety and protective appliances together by providing a combination comprising both eyeglasses and earplugs or earplugs alone which are adapted to be joined to eyeglasses. Combining the two appliances makes it less likely that a worker will misplace one or the other of them.

U.S. Pat. No. 3,943,925 provides earplugs intended to be inserted into the wearer's external auditory canals and the earplugs are adapted to be joined to eyeglasses. Short arms extending from eyeglass temple-mounted universal joints carry the earplugs; the arms and earplug axes make a fixed 90° angle. U.S. Pat. Nos. 4,902,120 and 5,404,385 are directed to eyeglasses which carry earphones for the reception of output from a cassette tape player or radio. The earphones in these combinations are not designed or intended to seal tightly into a wearer's auditory canals to exclude extraneous noise. U.S. Pat. Nos. 5,133,596 and 5,289,592 disclose combinations of eyeglasses with ear protection in the form of earmuffs, the eyeglass temple members being adjustable in length. Earmuffs do not present the same problems as earplugs and are not as effective as well-fitted earplugs in protecting against noise.

SUMMARY OF THE INVENTION

The earplugs adapted for joinder to eyeglasses and the combinations thereof provided by the prior art have not effectively addressed at least two problems associated with such assemblies.

In the first place, the designs of the earplug elements of the prior art fail to recognize that many wearers' external auditory canals do not lie at right angles to the sides of their heads. For these people, forcing the earplug elements of the eyeglass/earplug combinations of the prior art into the their external auditory canals can be extremely uncomfortable at best; at worst, poor seals of the earplugs to the external auditory canals results, leading to ineffective protection against noise as well as discomfort.

Secondly, the addition of earplugs to eyeglasses as provided in the prior art has done little or nothing to overcome or ameliorate the chronic eyeglasses problem, i.e. the tendency of the eyeglasses to slide down the nose of the wearer, a condition accentuated by perspiration. This problem is at its worst when eyeglasses protection is needed the most, on the job.

It is toward overcoming these and related problems that this invention is directed. Thus, it is one objective of this invention to provide an earplug assembly adapted for joinder to eyeglasses, as well as an eyeglass/earplug combination, in which each earplug element is free to assume the angle taken by an individual wearer's external auditory canal, thereby permitting a comfortable and effective seal against noise. It is a further objective in preferred embodiments of this invention to create a synergistic relationship between the eyeglass and earplug elements such that the tendency of the eyeglasses to slide down the nose of the wearer is substantially reduced. It is also an objective in preferred embodiments of the invention to provide for storage of the earplug element with the eyeglasses when the earplugs are not needed. It is yet an additional objective of the invention to provide an earplug assembly and an eyeglass/earplug combination which can be adjusted to fit the individual wearer. Additional objectives to be attained by the invention will become evident hereinafter.

In attaining these objectives, this invention provides as one aspect an earplug assembly adapted to be joined to eyeglasses, the assembly comprising a telescoping member which includes an elongated arm adapted at one end for connection to a temple of the eye glasses and sized to permit the other end to slide into a first end of an elongated, hollow collar for slidable engagement therewith, together with a hinge block carrying an earplug and a retained member, said retained member occupying a mating retainer at a second end of said collar for rotation in at least one plane containing the telescoping member. The rotation provided for the earplug relative to the longitudinal axis of the telescoping member allows the earplug to accommodate itself to the direction of the auditory canal into which it is inserted, providing a comfortable and secure seal against noise.

This invention provides as another aspect an eyeglass/earplug combination, one embodiment of which comprises a pair of eyeglasses having a right temple and a left temple, each of the two temples having joined to it one of the earplug assemblies described immediately above, the two earplug assemblies being mirror images of each other. Synergistic interaction between the eyeglasses and earplugs is created which counters the tendency of the eyeglasses to slide down the nose of the wearer.

Preferred embodiments of the earplug assembly and eyeglass/earplug combination aspects of the invention provide means whereby the length of the earplug assembly can be varied in steps to suit the individual wearer. Mechanisms are provided in other embodiments by which even greater freedom of the earplug to rotate relative to the primary axis of the telescoping member is provided. A variation of these embodiments provides a mechanism by which the earplugs can be retained out of the way on the temples of the eyeglasses when the earplugs are not required to be used.

The construction and uses of both aspects of this invention will be clarified by reference to the drawings which accompany this specification, the content of which is summarized immediately hereinafter, and to the detailed description which follows.

DETAILED DESCRIPTION

Figure 1:
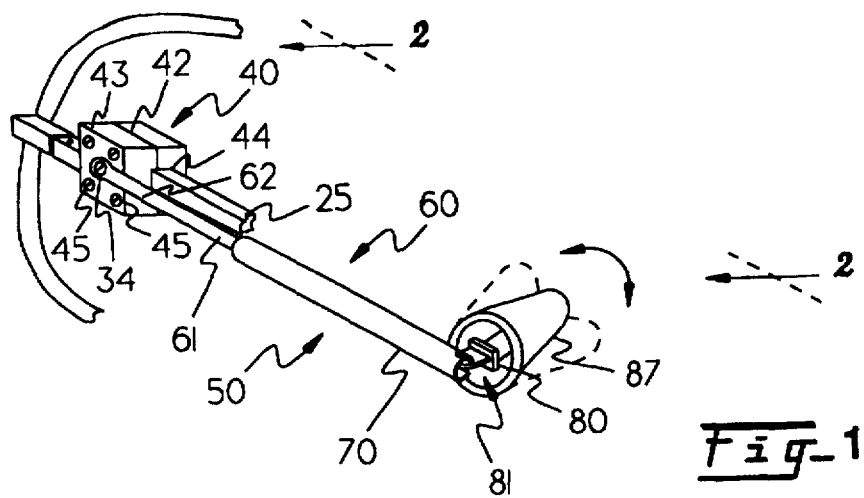
FIG. 1 is an isometric view showing a preferred embodiment of the earplug assembly aspect of this invention.

Attention is first directed especially to FIGS. 1–6, which illustrate preferred embodiments of the protective earplug assembly aspect of this invention, the earplug assembly being adapted for joinder to eyeglasses. A single earplug assembly is illustrated in these Figures. It will be understood, however, that two earplug assemblies are generally required to completely equip a pair of eyeglasses with ear protection. Since the two earplug assemblies are simply mirror images of each other, those skilled in the art will be able to construct both earplug assemblies readily from a description of either one of them.

Although other materials of construction may be advantageously used in some situations, aside from the rubbery material employed in earplug 87, it is preferred that the other major components of the earplug assembly be molded from thermoplastic, such as polyethylene or polypropylene, which is relatively soft, resilient, and to an extent, self-lubricating. Satisfactory rubber earplugs are available in commerce, and plastics fabricators can produce the plastic components.

The earplug assembly of this invention is adapted for joinder or connection to one of the temples of a pair of eyeglasses. A portion of a pair of eyeglasses is shown in phantom line in FIG. 1, earplug assembly 50 being adapted for connection to the left temple 25 of the eyeglasses. More particularly, telescoping member 60 includes elongated arm 61. One end 62 of the elongated arm carries adaptive fitting 63 for connection to temple 25.

There are a number of ways in which end 62 can be adapted for connection to temple 25. For example, elongated arm 61 can be molded as a part of temple 25 or tightly fastened thereto, establishing a rigid connection. On the other hand, the temple can be equipped with a ball and socket joint such as that disclosed in U.S. Pat. No. 3,943,925, for example, which provides a very flexible connection when elongated arm 61 to connected thereto.

However, it is preferred that end 62 be adapted for semi-rigid connection to temple 25 by including an adaptive fitting 63 which permits telescoping member 60 to turn in a single plane roughly paralleling the near side of the eyeglass wearer's head. An axial fastener 34, which pins end 62 and temple 25 together by passing through each member, achieves this objective, providing an axis perpendicular to which telescoping member 60 is free to turn; see, for example, FIG. 8. Suitable axial fasteners 34 include, for example, threaded devices, such as screws and bolt/nut combinations, as well as hollow rivets and solid pins.

An unexpected synergism between the eyeglasses and the earplugs is obtained when rigid or semi-rigid connections are established between the eyeglasses and the telescoping members which carry the earplugs. In these cases, when the earplugs are in use, i.e., inserted into the external auditory canals of the wearer, the tendency of the eyeglasses to slide down the nose of the wearer is dramatically reduced. A rigid connection achieved by molding elongated arm 61 as a part of temple 25 removes the degree of freedom achieved when these parts are simply pinned together with an axial fastener and makes it difficult to fit the eyeglass/earplug combination to a variety of different wearers. Thus, a semi-rigid connection is preferred. If axial fastener 34 is a threaded fastener, the rigidity of the connection can be adjusted as necessary to provide optimum performance.

Figure 8:
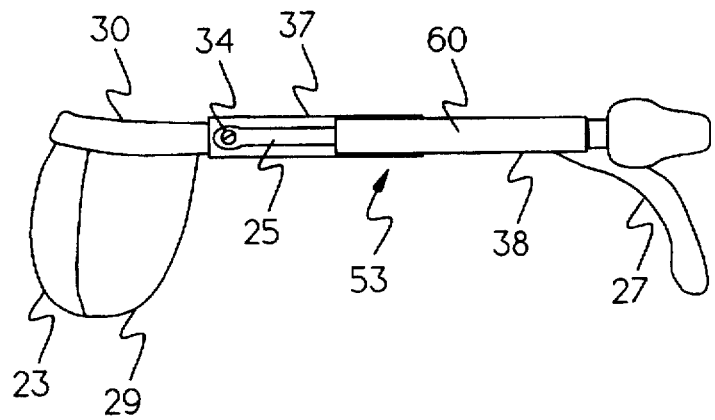
FIG. 8 is one elevation of a portion of the combination shown in FIG. 7.
Figure 9:
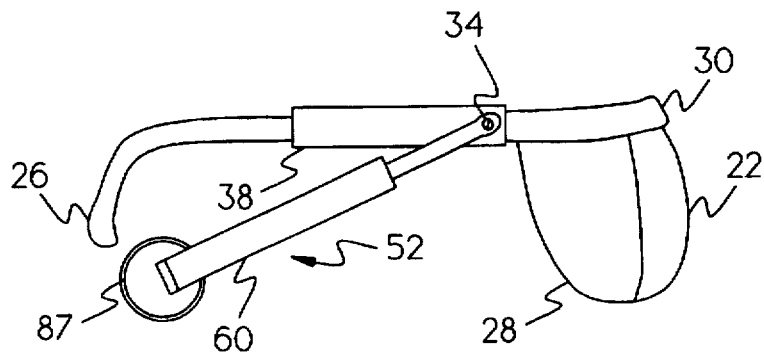
FIG. 9 is another elevation of a portion of the combination shown in FIG. 7.

It will be evident that in the preferred embodiment employing an axial fastener, adaptive fitting 63 will have a hole 66 through which to pass axial fastener 34. Although the adaptive fitting can be pinned directly to a temple 25, as shown in FIG. 8, for example, the preferred semi-rigid connection can also be achieved by joining adaptive fitting 63 to the temple via a temple mount, such as mount 40 shown in phantom line in FIG. 1. Mount 40, which is not part of this invention, could comprise, e.g., an inside member 42, and an outside member 43 channeled to create temple slot 44. Mount 40 could be rigidly affixed to temple 25 with fasteners 45, which could be threaded fasteners, for example. It will be evident that a number of variations in such a mount are possible without departing from the teachings and spirit of this invention.

Figure 7:
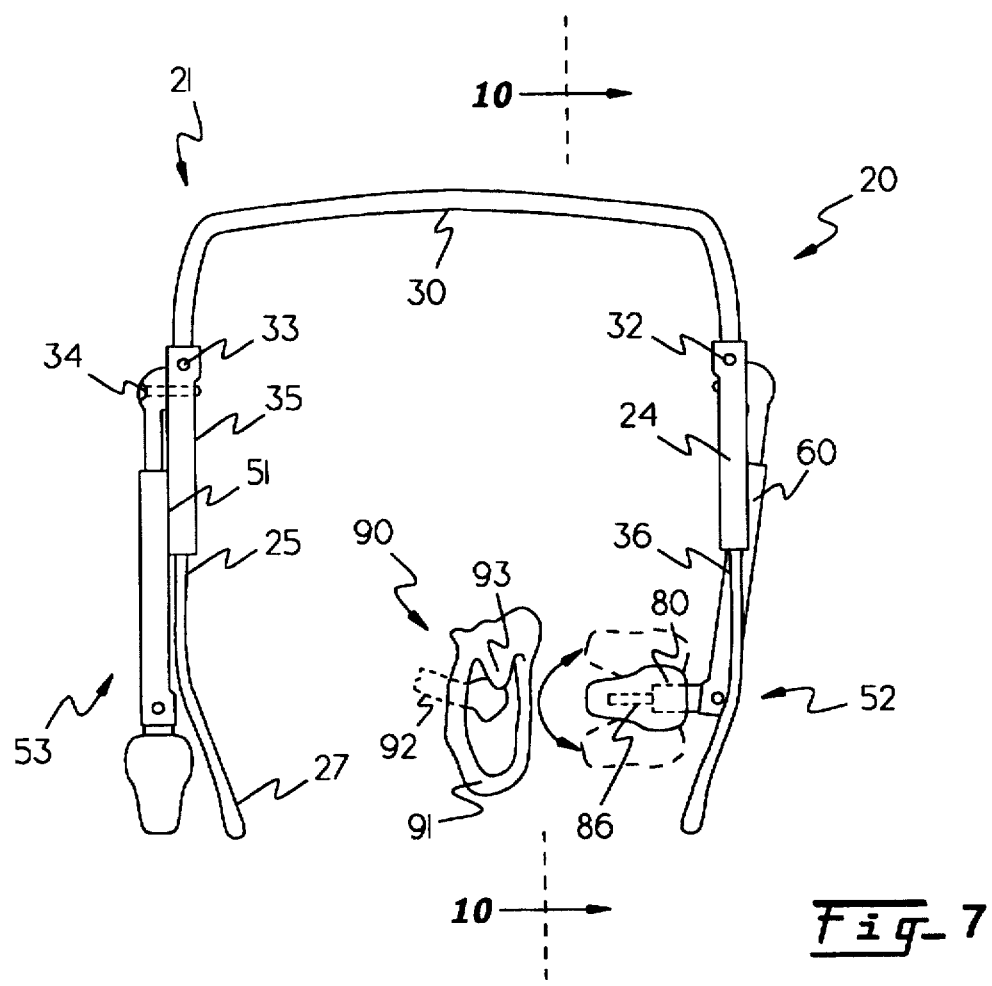
FIG. 7 is a plan view of a preferred embodiment of the eyeglass/earplug combination aspect of this invention.

Another feature of preferred embodiments of this invention can be realized as follows (see especially FIG. 5): One end 62 of elongated arm 61 has adaptive fitting 63. In addition to hole 66 passing through surface 64 which mates to temple 25, it is preferred that mating surface 64 and the longitudinal axis of elongated arm 61 not be parallel, but rather that the angle 65 between them be an obtuse angle. That is, it is preferred that angle 65 be, not 180° but, rather, about 160° to about 175°. Incorporation of this feature into the earplug assembly of this invention permits the earplug assembly to be stored, when not in use, alongside the eyeglasses to which it is joined, as shown in FIGS. 7 and 8, friction point 51 at the point of contact between left temple 25 and left earplug assembly 53 providing the holding force.

Figure 4:
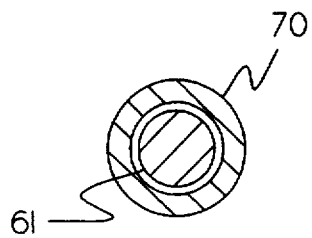
FIG. 4 is a cross-sectional view taken along line 4—4 in FIG. 3.
Figure 4A:
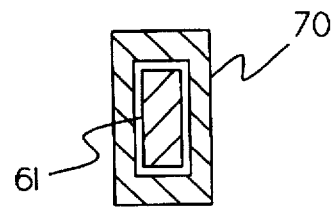
FIG. 4a is a cross-sectional view like FIG. 4 but showing an alternative embodiment.

As described above, one end 62 of elongated arm 62 is adapted for connection or joinder to a temple of a pair of eyeglasses. Elongated arm 61 is also sized to permit the other end 67 to slide into a first end 71 of elongated, hollow collar 70; see FIG. 5, for example. The fit should permit the elongated arm and collar to be joined together for slidable engagement, but snug enough to resist spontaneous lengthening or shortening of telescoping member 60. Sliding the elongated arm in the elongated, hollow collar permits the length of telescoping member 60 to be adjusted to fit the individual wearer. For largely aesthetic reasons, it is preferred that arm 61 and collar 70 be circular in cross-section, as shown in FIG. 4, but other cross-sections, such as the rectangular cross-section shown in FIG. 4a, for example, are satisfactory, it only being necessary that slidable engagement between these two members be provided.

Figure 2:
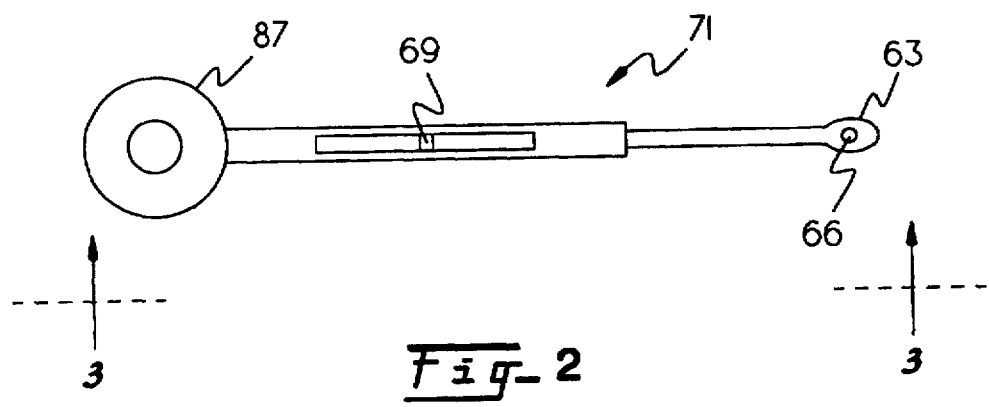
FIG. 2 is an elevation of the embodiment shown in FIG. 1 taken along line 2—2 in FIG. 1.
Figure 3:
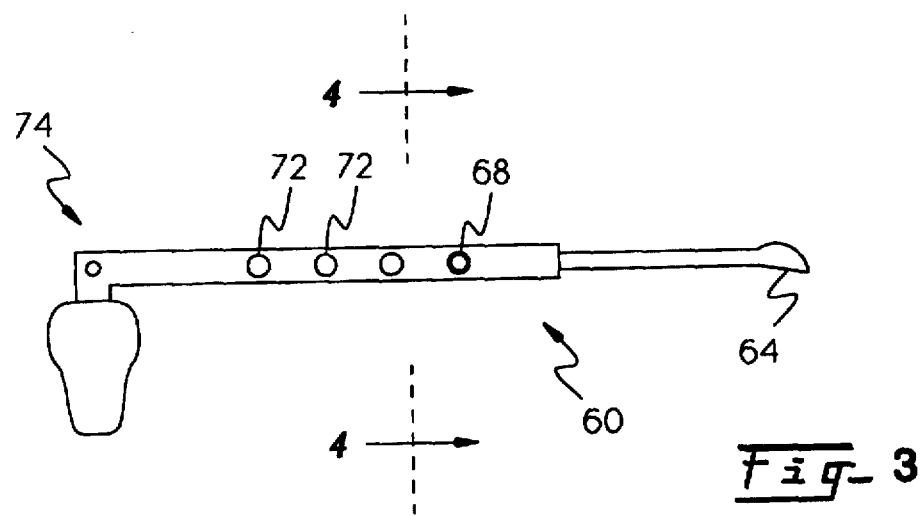
FIG. 3 is an underside view of the embodiment of FIG. 1 taken along line 3—3 in FIG. 2.

It may be desirable to ensure, especially if arm 61 is free to rotate within collar 70, that the range of motion of arm 61 in collar 70 be limited. This is achieved in preferred embodiments by providing a tooth 69 on arm 61 and a tooth slot 73 in collar 70 in which tooth 69 is retained. Furthermore, in preferred embodiments the lengthening and shortening of telescoping member 60 is restrained to occur in discrete steps. This can be achieved by adding protuberance 68 on arm 61 and a series of docking holes 72 in collar 70 to receive the protuberance. It is preferred for largely aesthetic reasons that one of the tooth slot and the series of docking holes be located on the underside and the other on the inside of telescoping member 60 as shown in FIGS. 2 and 3, for example. When elongated arm 61 and hollow collar 70 are made of thermoplastic material the elongated arm can be slid into the hollow collar readily even though the arm carries protuberance 68 and tooth 69 by simply warming one or both members, which causes them to soften slightly.

A hinge block 80 (see, e.g., FIGS. 1, 5 and 7) carries the earplug 87 mounted on plug support rod 86 and retained member 81. The hinge block, plug support rod and retained member can be molded in one piece from plastic if desired. Retained member 81 occupies a mating retainer 76 at the second end 74 of elongated, hollow collar 70 to turn or rotate in at least one plane containing telescoping member 60 as shown in phantom in FIG. 1.

Figure 5:
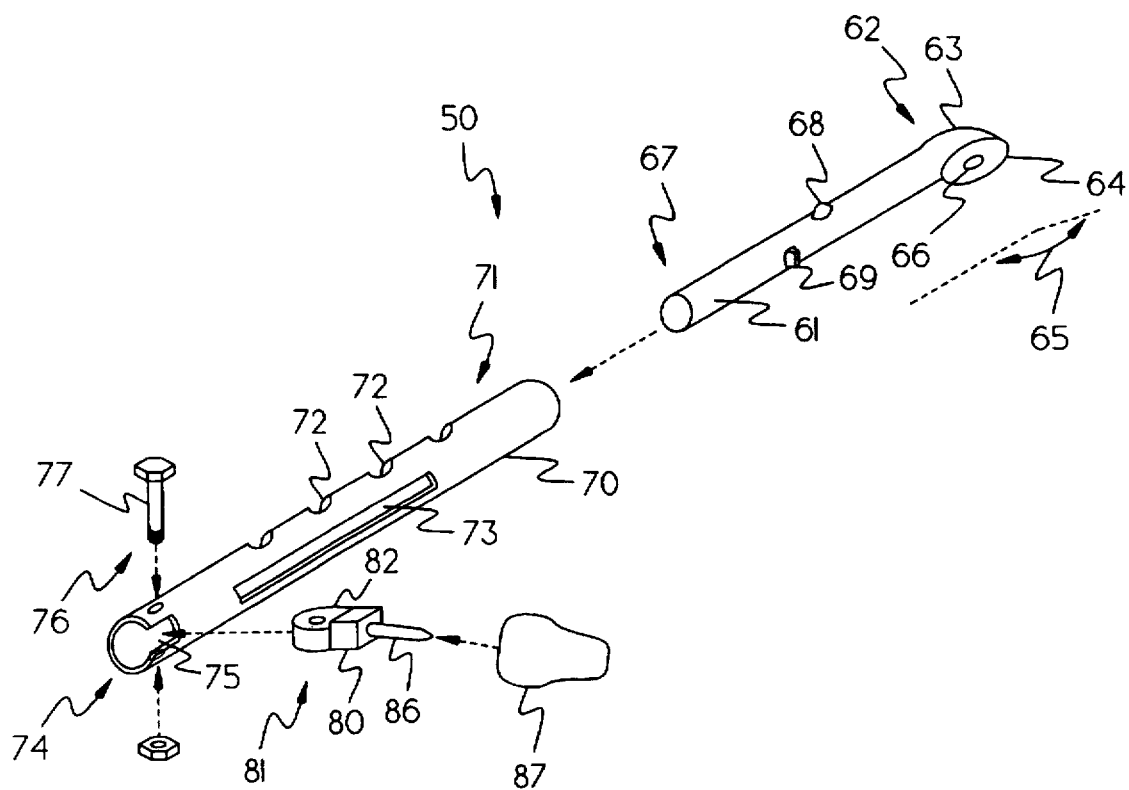
FIG. 5 is an illustrative isometric view showing the earplug assembly embodiment of FIGS. 1–4 with separated parts.

Although other mated retainer and retained elements are certainly possible, in a preferred embodiment shown in FIG. 5, the retained member is a hinge 82 and the retainer is a hinge pin 77, accessible through retainer slot 75, which can be a threaded fastener or equivalents thereof. The rotation of hinge 82, and consequently plug support rod 86 and earplug 87 are constricted to a single plane, perpendicular to hinge pin 77, a plane which also includes telescoping member 60.

Figure 6:
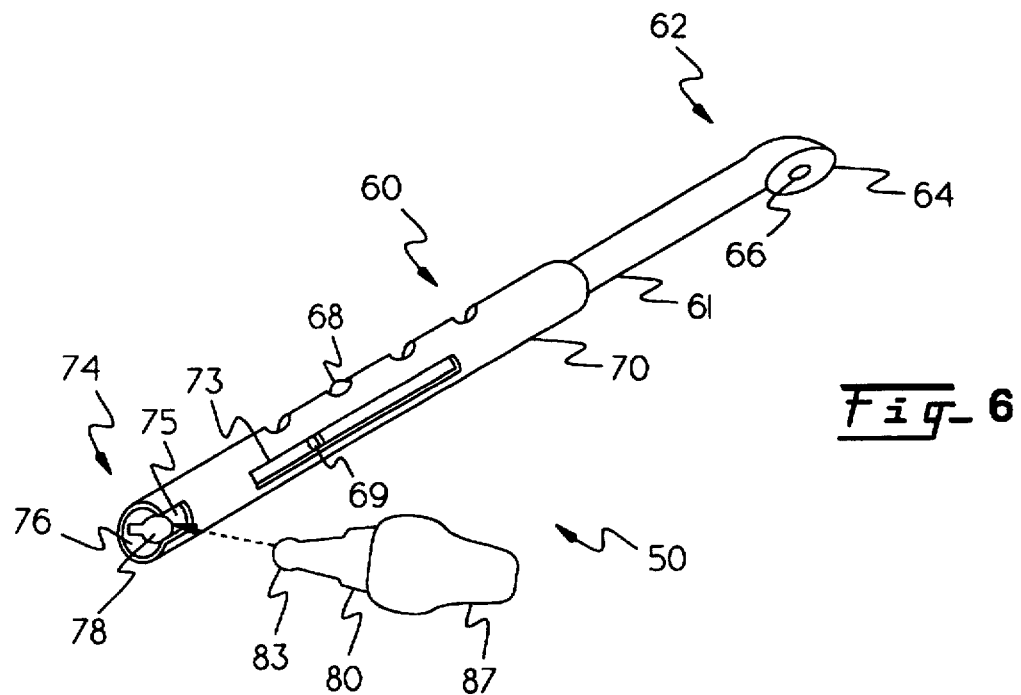
FIG. 6 is an illustrative isometric view like FIG. 5, but showing an alternative embodiment of the earplug assembly aspect of this invention with separated parts.

In an alternative embodiment of earplug assembly 50, the retained member and the mating retainer pair can be a ball and socket pair such as illustrated in FIG. 6. As shown, hinge block 80 carries a retained member, viz., ball-shaped extension 83, and the second end 74 of hollow collar 70 carries as mating retainer 76 a socket 78 which receives the ball 83. Retainer slot 75 in the hollow collar is provided for access in the embodiment shown, since the mating retainer is located within the second end 74 of the hollow collar. The retainer slot shown in FIGS. 5 and 6 is not required if the mating retainer 76 is added as an extension externally to hollow collar 70.

In the aforesaid embodiment, the ball and socket joint permits free rotation of the earplug element to accommodate insertion of earplug 87 into an external auditory canal but decreases somewhat the rigidity of the eyeglass/earplug combination. However, when the universal joint is at the second end of hollow collar 70, earplug 87 is connected by a very short lever arm to the universal joint, whereas the entire telescoping member 60 provides a much longer lever arm if the one end 62 of elongated member 61 is connected to the temple of the glasses via a universal joint. Thus, the detrimental effect of the flexible universal joint on the rigidity of the eyeglass/earplug combination is minimized when the universal joint is near the earplug end of the combination.

Figure 10:
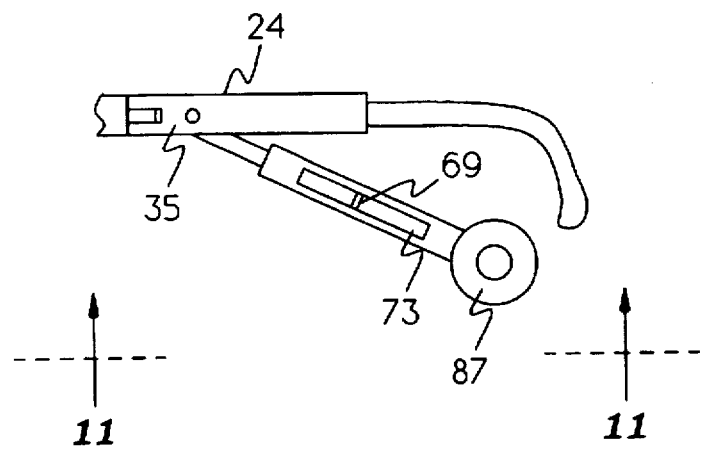
FIG. 10 is an elevation of a portion of the combination of FIG. 7 taken along line 10—10 in FIG. 7.
Figure 10A:
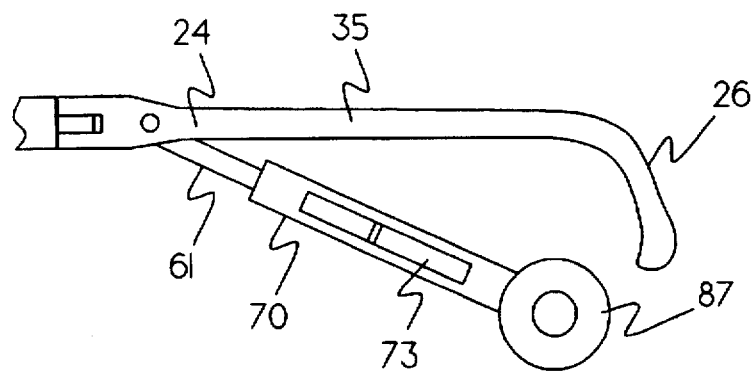
FIG. 10a is an elevation like FIG. 10 but showing an alternative embodiment.
Figure 11:
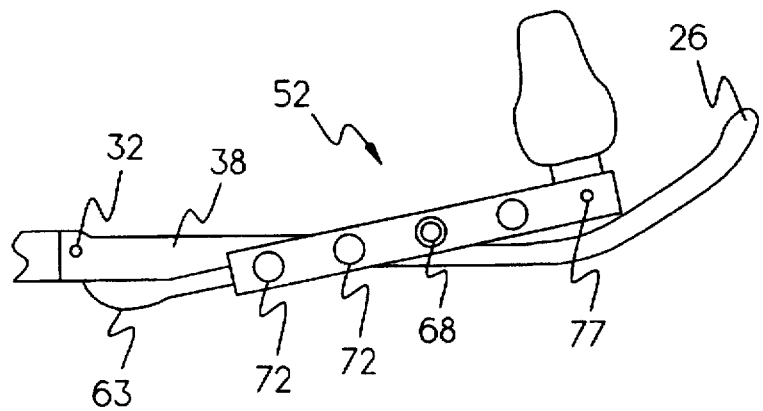
FIG. 11 is an underside view of the portion of the combination shown in FIG. 10 taken along line 11—11 in FIG. 10.
Figure 12:
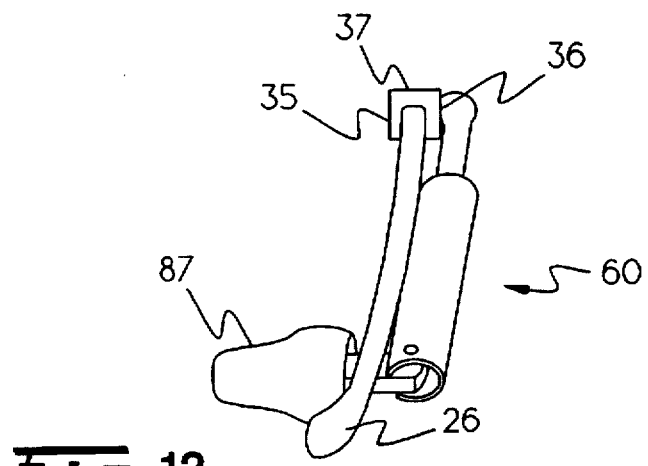
FIG. 12 is a rear elevation of the portion of the combination shown in FIG. 10.

The second aspect of this invention, an eyeglass/earplug combination employing the earplug assembly described hereinabove, is shown in FIGS. 7–12. Eyeglasses are known in which the temples are of variable length, and the earplug assembly of this invention is especially advantageous when such eyeglasses are employed in the combination, and such eyeglasses are illustrated in the figures. However, a combination of the earplug assembly of this invention with eyeglasses, such as those shown in FIG. 10a, having plain, unadjustable temples is also contemplated. Although the earplug assembly can be adapted to fit an arbitrary pair of eyeglasses, the earplugs will advantageously be joined to safety eyeglasses for use in the workplace.

A combination 20 of the eyeglass/earplug combination of this invention includes a pair of safety eyeglasses 21 having a frame 30 which holds right lens 22 and left lens 23, as well as right temple 24 terminating in right ear loop 26 and left temple 25 terminating in left ear loop 27. Safety glasses are often equipped with side protectors 28 and 29. The temples are joined to the frame by means of right temple screw 32 and left temple screw 33. Surface 35 is the inside of the temple, and surface 36 is the outside of the temple. Surfaces 37 and 38 are the upperside and underside of the temple, respectively. The earplug assemblies 52 and 53 are preferably joined to the temples 24 and 25, respectively, by means of axial fasteners 34 which permit telescoping members 60 to turn or rotate in a plane which roughly parallels the side of the wearer's head.

Earplug assembly 53 is shown stored alongside temple 25, it being held there by contact at friction point 51. Earplug assembly 52 is shown in a position whereby earplug 87 is poised for insertion into the wearer's external auditory canal.

FIG. 7 contains an illustration in phantom line of a human ear 90 with its auricle 91, its external auditory canal 92 and a cartilage flap 93, which is present as an anatomical feature of many human ears. When present, this flap prevents comfortable entry if the earplug is restrained to make a 90° angle with the side of a wearer's head, which substantially parallels temple 24 and telescoping member 60. It will be evident that a comfortable entry and properly sealed, comfortable retention can be provided if the earplug is free to turn or rotate as illustrated by phantom line in FIG. 7 in a plane which includes telescoping member 60.

Although the invention has been described by reference to specific preferred embodiments which are shown in the figures, it not intended that the invention be viewed as limited to the illustrated embodiments. Rather, the invention is limited only with reference to the following claims.

I claim:

1. An earplug assembly for connection to eyeglasses, the assembly comprising a telescoping member which includes an elongated arm adapted at one end for connection to a temple of the eyeglasses and sized to permit the other end to slide into a first end of an elongated, hollow collar for slidable engagement therewith, together with a hinge block carrying an earplug and a retained member, said retained member occupying a mating retainer at a second end of said collar for rotation in at least one plane containing the telescoping member; whereby the earplug accommodates itself to the direction of the external auditory canal into which the earplug is inserted.

2. The earplug assembly of claim 1 wherein said collar further includes a row of docking holes along its length to receive a protuberance carried by said elongated arm, thereby providing stepwise variation in the length of the telescoping member.

3. The earplug assembly of claim 1 wherein one of said retained member and said mating retainer is ball-like in shape and the other is a mating socket.

4. The earplug assembly of claim 1 wherein said retained member is a hinge passed through a retainer slot in said collar and retained by a hinge pin which passes through both the collar and the hinge.

5. The earplug assembly of claim 1 which further comprises a tooth slot in said collar to receive a tooth projecting from said elongated arm, thereby limiting the range of motion of the elongated arm in the collar.

6. The earplug assembly of claim 1 wherein the one end of said elongated arm is adapted for semi-rigid connection to the temple of said eyeglasses.

7. The earplug assembly of claim 6 wherein the adaptation is achieved by terminating the one end with an adaptive fitting having a mating face and provided with a hole through which to pass a fastener.

8. The earplug assembly of claim 7 wherein the mating face makes an obtuse angle with the telescoping member.

9. The earplug assembly of claim 1 wherein said telescoping member is round in cross-section.

10. An earplug assembly for connection to eyeglasses, the assembly comprising a telescoping member which includes an elongated arm adapted at one end for connection to a temple of the eyeglasses by terminating the one end with an adaptive fitting having a mating face and provided with a hole through which to pass a fastener, the mating face making an obtuse angle with the telescoping member, the elongated arm being sized to permit the other end to slide into a first end of an elongated, hollow collar for slidable engagement therewith; said collar having a row of docking holes along its length to receive a protuberance carried by said elongated arm to provide stepwise variation in the length of the telescoping member, as well as a tooth slot in said collar to receive a tooth projecting from said elongated arm to limit the range of motion of the elongated arm in the collar; together with a hinge block carrying an earplug which can project toward the ear of one wearing the combination and a retained member which is a hinge passed through a retainer slot at a second end of said collar and retained by a hinge pin which passes through both the collar and the hinge; whereby the earplug is rotatable in the plane containing the telescoping member and accommodates itself to the direction of an external auditory canal into which the earplug is inserted.

11. An eyeglass/earplug combination which comprises a pair of eyeglasses having a right temple and a left temple, each temple having connected to it an earplug assembly, the earplug assemblies being mirror images of each other; each earplug assembly comprising: a telescoping member which includes an elongated arm adapted at one end for connection to a temple of the eyeglasses and sized to permit the other end to slide into a first end of an elongated, hollow collar for slidable engagement therewith, together with a hinge block carrying an earplug and a retained member, said retained member occupying a mating retainer at a second end of said collar for rotation in at least one plane containing the telescoping member; whereby the earplug accommodates itself to the direction of an external auditory canal into which the earplug is inserted.

12. The combination of claim 11 wherein said collar further includes a row of docking holes along its length to receive a protuberance carried by said elongated arm, thereby providing stepwise variation in the length of the telescoping member.

13. The combination of claim 11 wherein one of said retained member and said mating retainer is ball-like in shape and the other is a mating socket.

14. The combination of claim 11 wherein said retained member is a hinge passed through a retainer slot in said collar and retained by means of a hinge pin which passes through both the collar and the hinge.

15. The combination of claim 11 which further comprises a tooth slot in said collar to receive a tooth projecting from said elongated arm, thereby limiting the range of motion of the elongated arm in the collar.

16. The combination of claim 11 wherein the one end of said elongated arm is connected semi-rigidly to the temple of said eye glasses for rotation in a single plane which is substantially parallel to the side of a wearer's head.

17. The combination of claim 16 wherein semi-rigidity is achieved by terminating the one end with an adaptive fitting having a mating face and provided with a hole in the fitting and a corresponding hole in the temple through which is passed a fastener.

18. The combination of claim 17 wherein the mating face makes an obtuse angle with the telescoping member; thereby permitting the earplug assembly, when not in use, to be retained by frictional contact between the telescoping member and the temple.

19. The combination of claim 11 wherein the eyeglasses are safety eyeglasses.

20. The combination of claim 11 wherein the temples are equipped with means for adjusting their length.

* * * * *